(12) United States Patent
Staats

(10) Patent No.: US 7,041,208 B2
(45) Date of Patent: May 9, 2006

(54) MICROFLUIDIC DEVICES AND METHODS FOR TWO-DIMENSIONAL SEPARATIONS

(76) Inventor: Sau Lan Tang Staats, 609 Ramsey Rd., Hockessin, DE (US) 19707

( * ) Notice: Subject to any disclaimer, the term of this patent is extended or adjusted under 35 U.S.C. 154(b) by 583 days.

(21) Appl. No.: 10/317,148

(22) Filed: Dec. 11, 2002

(65) Prior Publication Data
US 2003/0156993 A1  Aug. 21, 2003

Related U.S. Application Data

(60) Provisional application No. 60/378,881, filed on May 8, 2002, provisional application No. 60/338,696, filed on Dec. 11, 2001.

(51) Int. Cl.
  *G01N 27/447* (2006.01)
  *G01N 27/453* (2006.01)
(52) U.S. Cl. .......... 204/455; 204/605
(58) Field of Classification Search .......... 422/99, 422/100; 204/601–605, 451–455
  See application file for complete search history.

(56) References Cited

U.S. PATENT DOCUMENTS

| | | | |
|---|---|---|---|
| 5,938,906 A * | 8/1999 | Moi et al. | 204/465 |
| 6,136,171 A * | 10/2000 | Frazier et al. | 204/450 |
| 6,169,394 B1 * | 1/2001 | Frazier et al. | 324/71.4 |
| 6,221,654 B1 | 4/2001 | Quake et al. | |
| 6,268,219 B1 | 7/2001 | Mcbride et al. | |
| 6,321,791 B1 | 11/2001 | Chow | |
| 6,475,363 B1 | 11/2002 | Ramsey | |

FOREIGN PATENT DOCUMENTS

| | | |
|---|---|---|
| JP | 2762639 | 3/1998 |
| JP | 11-273044 | 10/1999 |

OTHER PUBLICATIONS

International Search Report for PCT/US02/39617.

\* cited by examiner

*Primary Examiner*—Alex Noguerola
(74) *Attorney, Agent, or Firm*—Darby & Darby

(57) ABSTRACT

A microfluidic device includes first and second substrates and a microfluidic cavity formed in one of the first and second substrates. The microfluidic cavity has a width (W) and a depth (D), wherein the other of the first and second substrates encloses the microfluidic cavity and a width (W) to depth (D) ratio is at least 100 with the depth (D) being from about 10 μm to about 150 μm. The device also includes a plurality of ports formed in the other of the first and second substrates to permit access to the microfluidic cavity and a third substrate disposed on the second substrate and including microchannels formed therein. The microchannels are formed so that a plurality of ports formed in the second substrate for sample selection and sample output communicate therewith.

21 Claims, 9 Drawing Sheets

MICROFLUIDIC DEVICES AND METHODS FOR TWO-DIMENSIONAL SEPARATIONS

CROSS-REFERENCE TO RELATED APPLICATIONS

This application claims the benefit of U.S. patent application Ser. No. 60/338,696, filed Dec. 11, 2001 and U.S. patent application Ser. No. 60/378,881, filed May 8, 2002, both of which are hereby incorporated by reference in their entirety.

TECHNICAL FIELD

This invention relates to microfluidic devices and techniques, and more particularly to microfluidic devices and methods to achieve protein separation based on charge and molecular weight or size.

BACKGROUND

For the past twenty years, 2-D gel electrophoresis has been the predominant technique for analyzing the protein constituents of whole cells and cell organelles. 2-D gel separates proteins based on the charge or pKa, i.e., the acidity and alkalinity, of the protein molecules on one axis, and molecular size on the other axis. Individual proteins in the gel are isolated as "spots," and further characterization of spots of interest may be carried out by excising the spot from the gel, and applying appropriate sample preparation procedures for analytical measurements.

This technique is notoriously difficult for many reasons. First, only a small fraction, a few percent, of the proteins in a cell show up as spots in the gel. Second, identifying the spot of interest in the gel in a typically extremely complicated spot pattern is difficult. Third, the protein to be isolated is tangled in the gel and needs to be removed from the gel by cutting it out and then dissolving in solvents. Fourth, reproducibility is poor, making it difficult to compare spots in two different gels. Fifth, the technique is extremely labor intensive, from pouring gels to finding differences among the numerous spots for different gels, to cutting and processing the separated proteins. Last but not least, quantitation of the proteins in the gel is nearly impossible.

The device and techniques described herein will overcome many of these difficulties.

SUMMARY

A microfluidic device is provided and includes a width to depth ratio of at least 100 and up to 50,000 or more, with the depth of the fluidic volume from 10 to about 150 μm. The present microfluidic devices differ from microfluidic devices in the prior art in that the microfluidic element used for separation is not a channel with a length to width ratio of over 1000. The microfluidic device also includes rows of orifices that are staggered to sample the fluidic content along the entire width of a microfluidic cavity formed in the device includes the gel and buffer input and output ports, and sample input and output ports. The microfluidic device is preferably made of polymer substrates that are substantially planar. A method with which this microfluidic device is used for the separation of protein molecules in two dimensions is also disclosed.

The microfluidic device disclosed herein is formed of two substrates. Fluid flows in spaces formed by the first and the second substrates. The microfluidic device structures allow non-permanent bonding of the two substrates by mechanical pressure alone. Thus this application reveals a microfluidic device with substrates that create the microfluidic features that are sealed using no heat or adhesive, which often generate undesirable side effects. The disclosed method and the present device allows users to assemble microfluidic devices with raised walls on one substrate and a corresponding insert on another substrate to create devices of designs that can be changed after each substrate has already been fabricated. The liquid tight seal of the microfluidic features is easily and conveniently obtained by any user of the device with a minimal requirement for dexterity.

The raised walls insert combination also improves liquid handling interface with external devices such as robotic liquid handling systems, and increases flexibility for detection technology. This microfluidic device is suitable for operations designed for functions including chromatographic and electrophoretic separations, including multidimensional separation in which the detection of the components in the fluid is by means of UV, visible light, fluorescence, chemiluminescence, scattering, etc., and by means of electrochemical and electroconductivity detection, or mass spectrometry. The microfluidic devices described herein are preferably made of polymer materials by injection or compression molding methods.

BRIEF DESCRIPTION OF THE FIGURES

All the figures are schematic drawings of the salient features of the microfluidic device disclosed in this invention. The features shown are not drawn to scale but are understood by those skilled in the art to represent the utility and features that distinguish this invention from prior art.

DETAILED DESCRIPTION OF PREFERRED EMBODIMENTS

A microfluidic device suitable for the two-dimensional separation of proteins from whole cells is provided and illustrated in a number of different embodiments in the present application. Each of the present microfluidic devices when used in such an application will allow high-resolution separations, quantitative detection of the separated protein spots, isolation of the desired separated protein molecules without entanglement in semi-solid gel, and potential integration of this two-dimensional separation step to other sample preparation steps before analysis by mass spectrometry.

Figure 1:
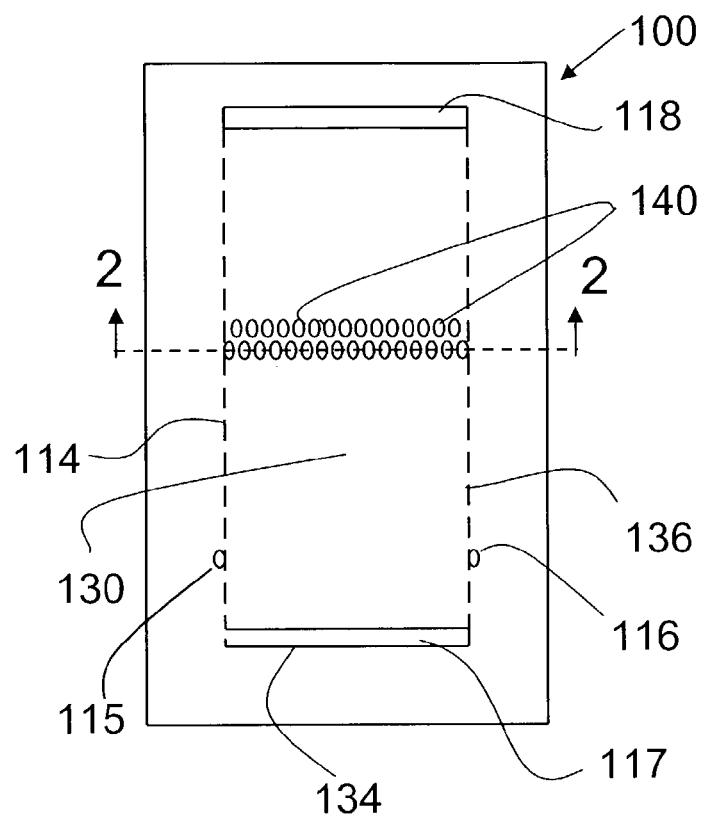
FIG. 1 is a top plan view of a microfluidic device according to a first embodiment and including a microfluidic cavity for multidimensional separation.
Figure 2:
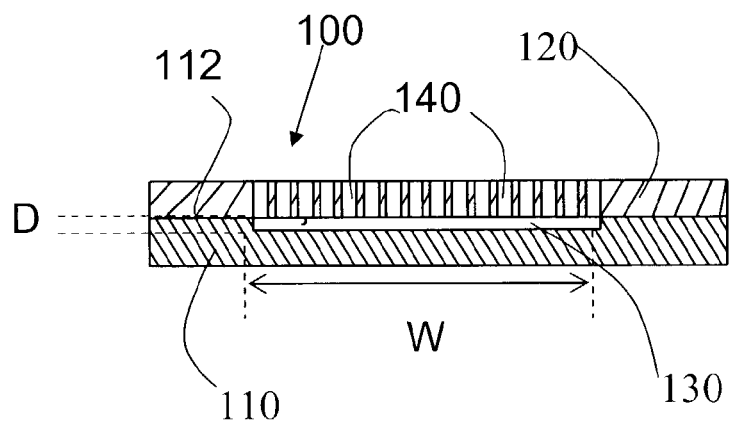
FIG. 2 is a cross-sectional view taken along the line 2—2 of FIG. 1.

Referring first to FIGS. 1–2 in which a microfluidic device 100 according to one exemplary embodiment is illustrated. The microfluidic device 100 includes a first substrate 110 and a second substrate 120. The first substrate 110 is constructed to serve as a base substrate and the second substrate 120 serves as a cover substrate as will be described in greater detail hereinafter. One exemplary first substrate 110 has a rectangular shape and includes a sample microfluidic cavity 130 formed therein. The microfluidic cavity 130 is a recessed section of the first substrate 110 such that it is partially defined by a floor 132 and a number of side walls and end walls. In the illustrated embodiment, the microfluidic cavity 130 has a rectangular shape and is defined by two opposing end walls 134 and two opposing side walls 136. The microfluidic cavity 130 is formed in a first face 112 of the first substrate and is only open on the first face 112. The first face 112 includes a peripheral border 114 formed by uppermost parts of the side walls 136 and end walls 134 that surround the recessed microfluidic cavity 130. It will be appreciated that the shape of each of the first and second substrates 110, 120 is not limited to the illustrated shape; but rather, each of the substrates 110, 120 can have any number of other shapes besides the rectangular shape that is illustrated. For example, the microfluidic cavity 130 can have an oblong shape, oval shape, etc.

Because the microfluidic cavity 130 is defined partly by a recessed section of the first substrate 110, it has a width (W) and a height or depth (D), as shown in the cross-sectional view of FIG. 2. The microfluidic cavity 130 serves as the microfluidic feature in the microfluidic device 100 in which fluid (sample) flows and in contrast to conventional microfluidic devices that have channels to carry the sample, the microfluidic cavity 130 is more of a chamber defined by a volume, as opposed to a channel that has much smaller dimensions. In one exemplary embodiment, the microfluidic cavity 130 has an aspect ratio of width (W) to depth (D) of at least 100, with the depth (D) being from about 10 μm to about 150 μm and preferably, from about 10 μm about 150 μm. The upper limit of the width (W) to depth (D) aspect ratio is chosen to optimize the charge or pKa separation, and may be as high as about 50,000 or as high as the manufacturing method allows.

The microfluidic cavity 130 is substantially enclosed since the second substrate 120 is disposed on the first face 112 of the first substrate 110, thereby acting as a ceiling for the microfluidic cavity 130 and enclosing the microfluidic cavity 130 so that the volume thereof can be determined. One or more and preferably a number of openings or ports are provided in the microfluidic device 100 to provide access to the microfluidic cavity 130. For example, the microfluidic cavity 130 is enclosed except where there are openings or ports for input and waste of sample, buffer/gel and other components needed to perform the method of operation of the fluidic device 100. In one exemplary embodiment, the microfluidic device 100 includes a sample input port 115, a sample output port (waste port) 116, a buffer and gel input port 117, and a waste port 118 for the buffer and gel. Preferably, the sample input port 115 and the sample output port 116 are formed at or near one end wall 134 of the microfluidic cavity 130 in an arrangement where the sample input port 115 is formed near or at one side wall 136 and the sample output port 116 is formed near or at the opposite side wall 136. In other words, the sample input port 115 and the sample output port 116 are formed on opposite ends of the width (W) of the microfluidic cavity 130. The buffer and gel input and output ports 117, 118 are formed on opposite ends of the length of the microfluidic cavity 130. More specifically, the buffer and gel input port 117 is formed at one end wall 134 of the microfluidic cavity 130 and the buffer and gel output port 118 is formed at the opposite end 118 of the microfluidic cavity 130. Each of the input ports 115, 117 and output ports 116, 118 communicate with the microfluidic cavity 130 so that sample and/or other material can be added or withdrawn therefrom. The input ports 115, 117 and output ports 116, 118 are formed in the second substrate 120 that acts as a cover.

The microfluidic device 100 also includes a series of openings or ports 140 for sample selection and sample output. The openings 140 are formed through the second substrate 120 such that they communicate with the microfluidic cavity 130. More specifically, the openings 140 are formed in the second substrate 120 along the width (W) of the microfluidic cavity 130 between the gel and buffer input port 117 and the gel and buffer output port 118.

It will be appreciated that the microfluidic volume of the microfluidic cavity 130 is defined by the first and second substrates 110, 120 that are two substantially planar substrates disposed against one another. In one embodiment, the microfluidic cavity 130 is a depression or recessed section with the aspect ratio of width to depth in the range described above fabricated with a variety of techniques known in the art on one surface of the first substrate 110, and is covered by the second substantially planar substrate 120 which contains the ports/openings for sample 115, 116 and fluidic input and output and sample selection 140.

Figure 3:
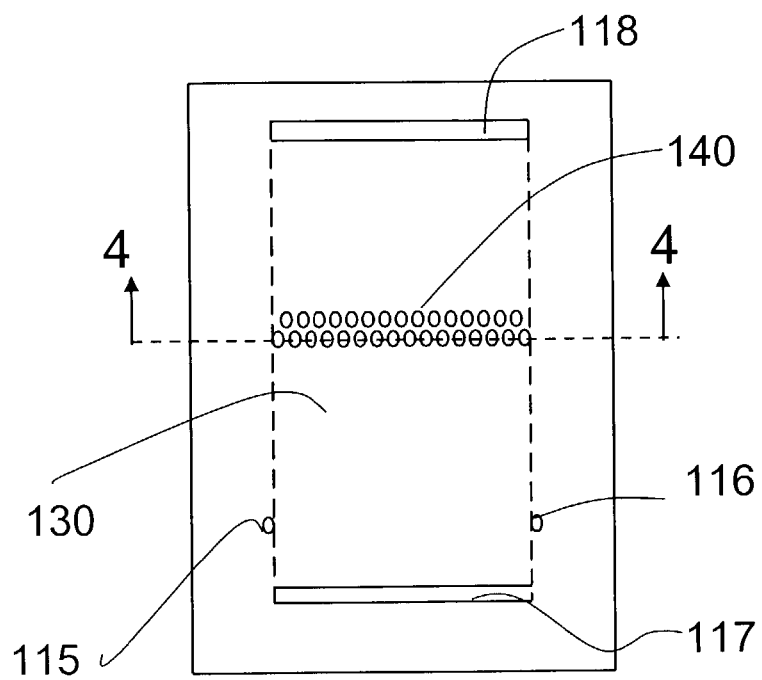
FIG. 3 is a top plan view of a microfluidic device according to a second embodiment and including a microfluidic cavity for multidimensional separation.
Figure 4:
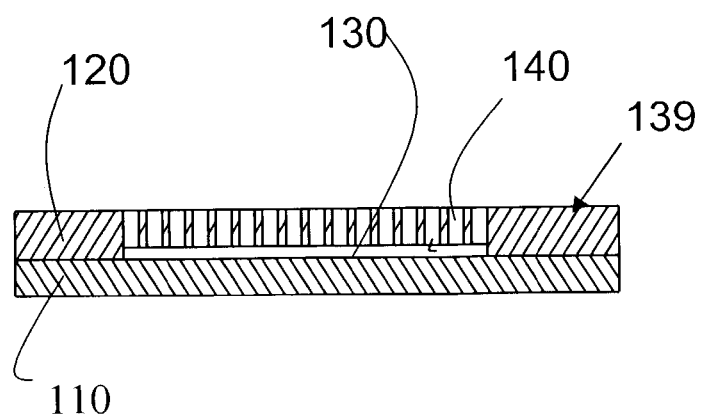
FIG. 4 is a cross-sectional view taken along the line 3—3 of FIG. 3.

In a second embodiment illustrated in FIGS. 3 and 4, the microfluidic device is fabricated so that the first substrate 110 includes both the microfluidic cavity 130 and the ports/openings 115, 117 and the other planar substrate 120 is bonded to the one planar substrate 110 as a cover. More specifically, the second planar substrate 120 does not have any openings or depressions formed therein and instead has two planar faces. The microfluidic cavity 130 is formed in one face 113 of the first substrate 110 and the ports/openings 115–118 and 140 are formed in a second face 139 such that they communicate with the microfluidic cavity 130. The dimensional aspects (e.g., aspect ratio) of the microfluidic cavity 130 are the same in this embodiment as they are in the first embodiment.

Figure 5:
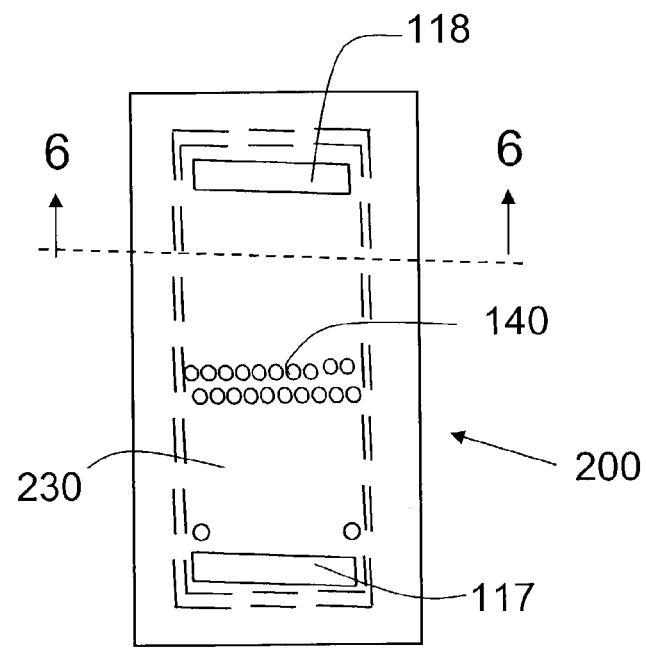
FIG. 5 is top plan view of a microfluidic device according to a third embodiment and including a microfluidic cavity for multidimensional separation.
Figure 6:
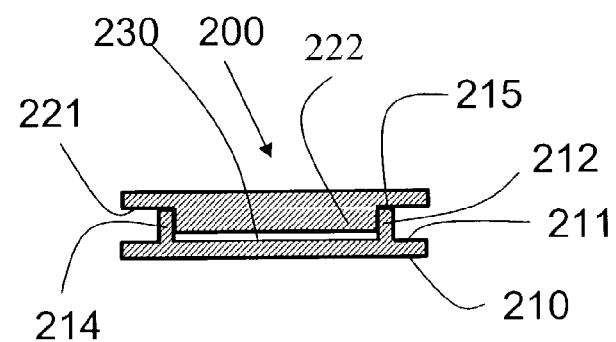
FIG. 6 is a cross-sectional view taken along the line 5—5 of FIG. 5.

FIGS. 5 and 6 show yet another embodiment in which a microfluidic device 200 is provided. The microfluidic device 200 includes a first substrate 210 and a second substrate 220. The first substrate 210 has a raised structure 212 that protrudes from a first face 211 of the first substrate 210 to at least partially define a microfluidic cavity 230. In one exemplary embodiment, the raised structure 212 is in the form of a pair of opposing side walls and end walls 214 that are joined together to at least partially define the microfluidic cavity 230. The use of raised walls 214 has been described in several earlier applications, including U.S. patent application Ser. No.: 10/061,001 and International PCT application serial No.: PCT/US02/02927, both of which are hereby incorporated by reference in their entirety. The second substrate 220 is constructed so that it includes a raised section 222 protruding from a first face 221 that is of a complementary shape as the microfluidic cavity 230 so that the raised section 222 is received within the raised structure 212 to enclose and partially define the microfluidic cavity 230. In other words, the dimensions of the raised section 222 are such that it is frictionally fit within the raised structure 212 in a manner that the microfluidic cavity 230 is sealed, with typically less than 25 μm tolerance.

The dimensions of the raised section 222 and the raised structure 212 control the overall volume of the microfluidic cavity 230 since the microfluidic cavity 230 is defined as the area therebetween. As best shown in FIG. 6, when the first and second substrates 210, 220 mate together, an upper edge 215 of the side and end walls 214 seats against the first face 221 of the second substrate 220. When the upper edge 215 seats against the first face 221, the raised section 222 does not seat against the first face 211 of the first substrate 210, thereby defining the microfluidic cavity 230 (which is the gap between the raised section 222 and the first face 211). Thus, it will be appreciated that by varying either one or both of the height of the end and side walls 214 or the height of the raised section 222, the volume of the microfluidic cavity 230 can be varied. For example, decreasing the height of the raised section 222 while maintaining the height of the side and end walls 214, increases the volume of the microfluidic cavity 230. While, the exemplary microfluidic device of FIG. 6 shows the width of the first and second substrates 210, 220 being the same or substantially the same, it will be appreciated that this does not have to be the case and in fact one of the substrates 210, 220 can have a width that is different from the other substrate 210, 220 so long as the microfluidic cavity 230 is sealed. In the previous applications mentioned above, a great improvement of the raised wall structures with a lid is that they offer far more secure bonding between the first and second substrates because the tight mechanical fit of less than 25 microns between the two substrates. Various configurations of the raised walls-lid combination can be used, although only one such combination is used as an exemplary embodiment in FIGS. 5–6.

In the present embodiment, a liquid tight seal can be obtained by applying pressure between the two substrates with the lid structure inserted into raised wall region without the use of glue or heat to further secure the two substrates 210, 220. The pressure is preferably applied directly over the area of the substrate where the upper edge 215 of the raised walls 214 contact the second substrate 220. The thickness of the raised walls 214 can be from about 500 μm to several thousand μm or more if no other support features are present to withstand the applied pressure. The height of the raised walls 214 can be in the range between about 25 microns to millimeters or more. The insert structure (raised section 222) can have a height that varies from about 25 μm to millimeters or more. The critical criterion for the height dimensions for microfluidic applications is that the difference in heights between the raised walls 214 and the insert (raised section 222) is smaller than about 200 μm if lamina flow is desired. If other support structures, such as pillars, are present between the two substrates 210, 220, then the thickness of the raised walls 214 can be reduced to below 500 μm. The mechanism for applying the pressure can be an appropriate mechanical clamping mechanism. When the pressure is released, the two substrates 210, 220 can be taken apart. This non-permanent liquid-tight bonding feature facilitates user-defined surface treatment methods to be applied to these devices when the two substrates 210, 220 are apart. If the microfluidic cavity 230 is preferred to be permanently sealed and the clamping mechanism on the device 200 during usage is not desired, the mechanical fit between the region formed by the raised walls 214 and the structure (raised section 222) inserted into the raised walls 214 to form the lid is increased to a tighter tolerance of less than 10 μm, i.e., the difference in widths between the separating distance between the two raised walls 214 and the width of the raised section 222 is within about 10 microns or so. This is termed an interference fit. The raised section 222 (lid structure insert) has to be pressed into the raised wall region.

Figure 7:
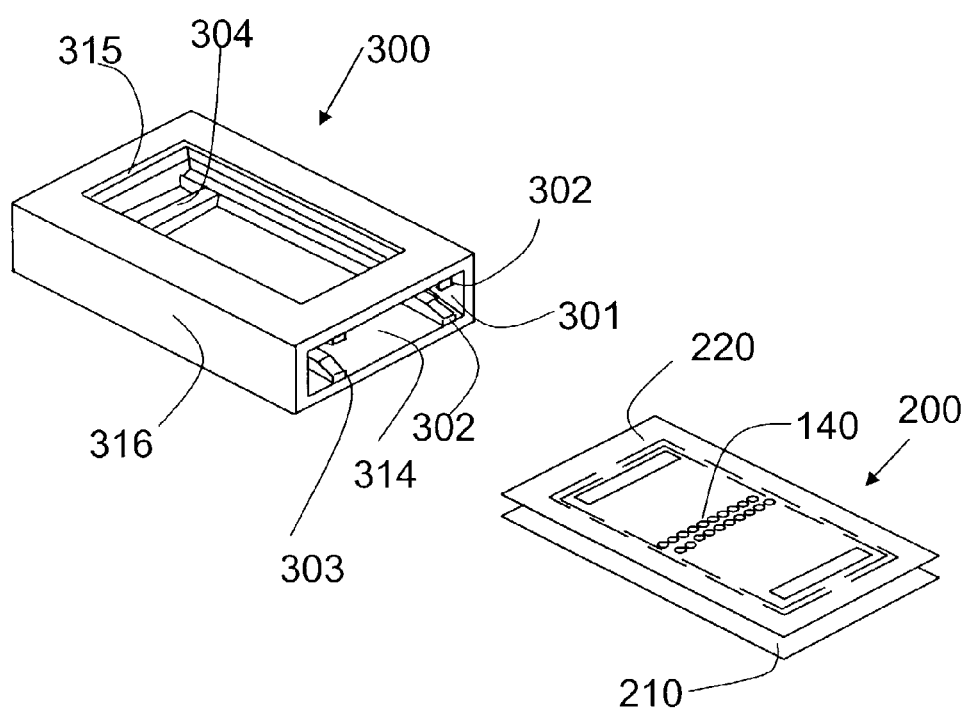
FIG. 7 is a perspective view of a cartridge for holding the microfluidic device of FIG. 5, which is shown removed therefrom.

Now referring to FIG. 7 in which another aspect of the present invention is illustrated. FIG. 7 illustrates a cartridge device 300 that is configured to apply the optimal pressure to the microfluidic device 200 (FIGS. 5 and 6) with a mechanical sealing feature when the microfluidic device 200 is inserted or placed into the cartridge device 300. The cartridge device 300 can be in the form of a pocket, as shown in FIG. 7 that receives the microfluidic device 200 through an opening 301. More specifically, the cartridge 300 has a body formed by opposing top and bottom walls 314 and side walls 316. At least the top wall 314 includes an opening 315 formed therein which aligns with one substrate face of the microfluidic device 200 to permit access to ports and openings formed therein. In the illustrated embodiment, the opening 315 has a rectangular shape similar to the rectangular shape of the microfluidic device 200.

The cartridge 300 also has a number of rails or ridges formed therein to locate and assist in retaining the microfluidic device 200 within the cartridge 300. For example, the cartridge 300 can include a plurality of longitudinal rails/ridges 302 and a plurality of transverse rail/ridge 304. Preferably, an inner surface of each of the top and bottom walls 314 includes a pair of spaced longitudinal rails 302 that extend substantially the length of one of the top and bottom walls 314. The pair of transverse rails 304 extend across the cartridge 300 between two opposing longitudinal rails 302 at each end of the cartridge 300. The longitudinal rails 302 and the one or more transverse rails 304 are formed on the cartridge 300 at places that correspond to the locations of the raised walls 214 that define the microfluidic cavity 130. In other words, the microfluidic device 200 is inserted into the cartridge 300 between one pair of longitudinal rails 302 formed on an inner surface of the top wall 314 and an opposite pair of longitudinal rails 302 formed on an inner surface of the opposite bottom wall 314. A clamping force is generated by the raised rails 302, 304 with a height of about 25 μm or more, and of about the same dimensions and shapes of the raised walls 214 in the microfluidic device 200 so that when the cartridge 300 is installed on the microfluidic device 200, the raised rails 302, 304 associated with the cartridge 300 exert mechanical pressure on the areas of the raised walls 214 in the microfluidic device 200 will become liquid tight. The clamping force results from the fact that the distance between the top surfaces of the upper and lower transverse rails 304 and the longitudinal rails 302 is slightly smaller than the thickness of the assembled device 200.

Ends 303 of the longitudinal rails 302 near the opening 301 have a chamfered construction to facilitate receipt of the substrates 210, 220 between the rails 302, 304. According to an exemplary application, the microfluidic device 200 is assembled outside of the cartridge 300 in the manner mentioned hereinbefore. In other words, the raised section 222 (FIG. 6) is received between the raised walls 214 to define the microfluidic cavity 230 and the two substrates are tightly fit together. By then inserting the microfluidic device 200 into the opening 301 of the cartridge 300 and then directing the microfluidic device 200 toward the closed end of the cartridge 300, a clamping force is applied by the raised rails 302, 304 against the first and second substrates 210, 220. More specifically, the force is applied by the raised rails 302, 304 in the areas where the raised walls 214 of the microfluidic device 200 exist, thereby ensuring that a seal around the microfluidic cavity 230 results between the first and second substrates 210, 220.

As previously mentioned, the first substrate 210 is visible through the opening 315 in the cartridge to permit the user to access the openings 140 formed in the microfluidic device 200. This is to permit the user to perform standard testing and detection operations by having access to the sample contained within the microfluidic cavity 230. The cartridge 300 can have other ports that allow the microfluidic device 200 within it to have access to sample, buffers, etc. placed outside of the device 200, and access ports for optical window, nozzle for electrospray and pipetting within the device to reach the outside world without interfering with the normal functions of these device features. During use, the microfluidic device 200 and the clamping cartridge 300 are used as one piece. The cartridge 300 is reusable and therefore, after the testing has been completed, the device 200 is removed from the cartridge 300 and another device 200 is inserted at the time of the next use.

The specific detailed design of the cartridge 300 varies with the microfluidic device 200 that it is designed to hold but each cartridge 300 will have the general features described above. The distance between the rails 302, 304 is chosen so that an optimal pressure is exerted on the device 200 to achieve the liquid seal of the microfluidic cavity 230.

Figure 8:
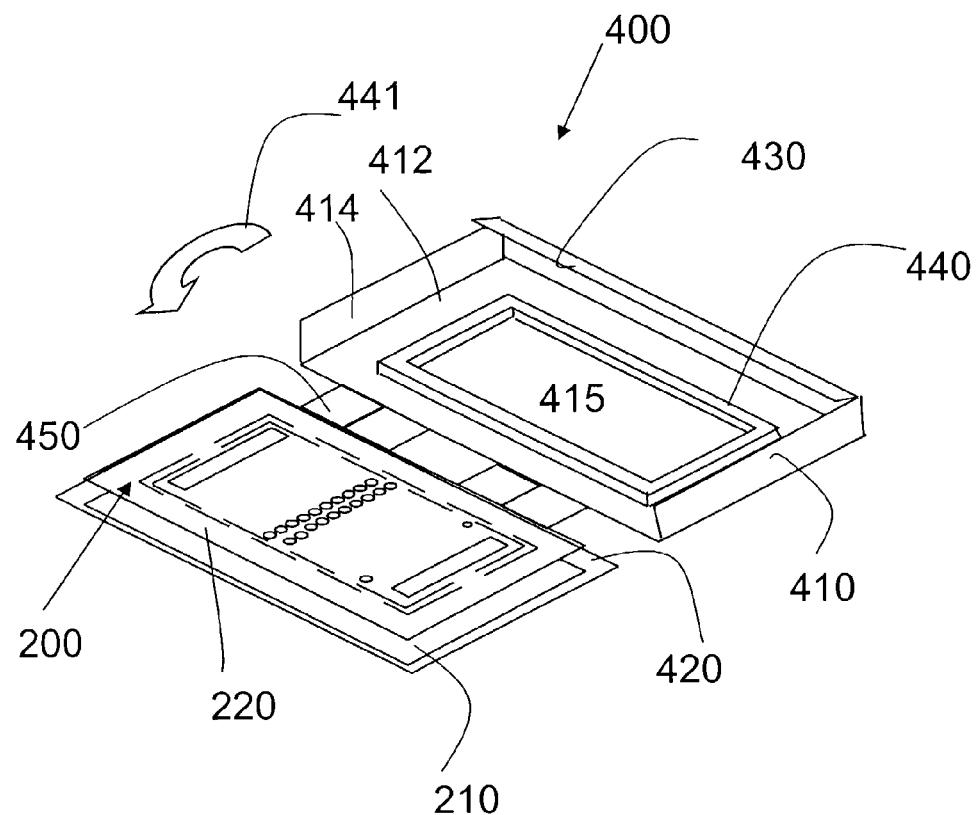
FIG. 8 is a perspective view of a cartridge according to another embodiment for holding the microfluidic device of FIG. 5, the cartridge being shown in an open position.

FIG. 8 is a perspective view of a cartridge 400 according to another exemplary embodiment. The cartridge 400 includes a first part 410 and a second part 420 that is hingedly connected to the first part 410 such that the cartridge 400 is positionable between an open position for receiving the microfluidic device 200 (FIGS. 5 and 6) and a closed position in which the microfluidic device 200 is securely held within the cartridge 400. The first part 410 serves as a base of the cartridge 400 and is defined by a floor 412 and side walls 414 that extend around substantially the entire periphery of the floor 412 with the exception that one side of the floor 412 does not have an associated side wall 414. Thus, in the illustrated embodiment where the floor 412 has a rectangular shape, three sides have three associated side walls 414, while the fourth side is left open. The fourth side is where the hinging action occurs. Preferably, the side walls 414 are perpendicularly orientated relative to the floor 412 and one of the side walls 414 has a latch member 430. More specifically, the side wall 414 that is across from the fourth open side of the floor 412 contains the latch member 430 which serves to latch or releasably secure the first and second parts 410, 420 to one another.

The first part 410 also includes a feature for exerting pressure directly over the raised walls 214 of the microfluidic device 200. This feature consists of a rail/ridge construction 440 formed on the floor 412 in the shape and dimensions of the raised walls 214 of the microfluidic device 200. In the illustrated embodiment, the rail construction 440 has a rectangular shape that mirrors the rectangular shape of the raised rails 214 of the microfluidic device 200. The first part 410 also has an opening 415 formed therein within the boundaries of the rail construction 440 for buffer and sample access and other observations.

The second part 420 is a plate-like member and serves as a cover for the cartridge 400 when the first and second parts 410, 420 are closed, the second part 420 is opposite the floor 412 with the microfluidic device 200 being disposed therebetween. In the illustrated embodiment, the second part 420 is a planar rectangular cover that seats against the side walls 414 of the cartridge 400. The second part 420 has dimensions that are greater than the dimensions of the microfluidic device 200 so that the microfluidic device 200 can be disposed on the inner surface of the second part without extending over any of the edges thereof.

It will be appreciated that the second part 420 can have locating features that serve to locate and hold the microfluidic device 200 on the second part 420 prior to closing the first and second parts 410, 420. For example, the locating features can be in the form of two or more locating posts or nubs that are formed on an inner surface of the second part 420. The microfluidic device 200 is placed on the inner surface of the second part 420 such that it is held between the nubs which are formed so that when the first and second parts 410, 420 are closed, the rail construction 440 aligns with the raised rails 214 so that the desired pressure is applied to the raised rails 214 when the cartridge 400 is closed.

The first and second parts 410, 420 are hingedly connected using conventional techniques. For example, a hinge 450 can be provided between the first and second parts 410, 420 to permit a pivoting action therebetween. It will be understood that hinge 450 can be a series of hinges that are connected at different locations along the fourth edge as illustrated in FIG. 8.

In use, the assembled microfluidic device 200 is first placed on the inner surface of the second part 420 at a location that will result in the raised walls 214 being aligned with the raised construction 440 when the first and second parts 410, 420 are closed. The first part 410 is then pivoted or folded, in the direction of arrow 441, toward the second part 420. The clasping edge 430 of the first part 410 clasps onto an edge of the second part 420 when the two parts 410, 420 are closed together, and the rail construction 440 of the first part 410 exerts pressure on the raised rails 214 (FIG. 6) of the microfluidic device 200 to create a liquid tight volume within the raised wall boundaries 214 of the device 200 (i.e., the microfluidic cavity 230 is sealed in a liquid tight manner). In this closed position, the user can access the microfluidic device 200 through the opening 415 formed in the second part 420 as illustrated in FIG. 8. Advantageously, both the cartridges of FIGS. 7 and 8 can be reused as the user simply needs to remove the spent microfluidic device after use and then prepare the cartridge for another use.

In another aspect, surface structures are provided on the surfaces of the raised walls 214 and the inserted structure (raised section 222) that will facilitate the seal. A mirror finish of these surfaces is generally desired, although a roughened finish may also be used. The roughened surface finish is analogous to the surface finish of a ground glass joint in chemistry glassware. A very thin film of chemically inert lubricant, such as silicone-based compounds used as stop-cork grease on ground glass joints in chemistry glassware, can also be applicable to some of the applications using these devices.

The liquid seal between the raised walls 214 and the raised section 222 (insert) is formed by pressure applied by clamping forces provided by external clamping mechanisms. Such mechanisms can be provided by common clamps such as what is commonly known as "butterfly" clamps for clipping a stack of paper, or by a custom designed cartridge as described above with reference to FIGS. 7 and 8. Because of the large width to depth ratio of the present microfluidic feature (microfluidic cavity 230), additional pressure exerted at additional points on the surface directly above the microfluidic feature itself may be applied to achieve depths of the microfluidic feature that are different from the device as fabricated. The flexing of the polymer in the substrate changes the depth dimension of the microfluidic feature. The degree of the flexing of the polymer with a given applied pressure is a material property of the polymer, and may be chosen to obtain the desired flex. For example, a flexing of the Topas TM 8007 grade of polycyclic olefin/polyethylene co-polymers is such that a substrate of about 1/16 of an inch thick may change the depth of the microfluidic feature from a depth of 200 microns to 100 microns with relatively mild clamping pressure as provided by that of a "butterfly" paper clip. The resulting depth of the feature with this applied pressure may be measured by putting a drop of liquid of known volume, e.g., 1 microliter, onto the several locations of the surface within the raised walls of the microfluidic feature, and then putting the substrate with the insert into the raised walls region and clamp at the raised walls as described herein. The areas of the drops of the known volume are now measured. The depth of the microfluidic feature is calculated to be the volume of the liquid divided by the area of the liquid between the two substrates. As additional pressure is exerted on the outside surface of the microfluidic feature, the area of each drop of the liquid will increase because the depth has been decreased. The new depth of the microfluidic feature may now be calculated. Using such a device, a microfluidic feature may be switched from lamina flow to non-lamina flow by appropriately varying the depths of the feature. Likewise such a device provides a convenient device to optimize the depth dimension of the microfluidic feature for a specific application.

The devices disclosed in this invention are preferably fabricated with thermoplastics using injection molding or compression molding. The polymers generally suitable for injection and compression molding have been described in the previous applications cited here and are included here. The preferred thermoplastic polymers are polybutylteraphalate, polycyclic olefin-polyethylene co-polymers and polyethylenes, polypropylenes and the like with little or no additives, which are preferred to maintain chemical purity of the devices. If optical transparency is needed, optical thermoplastics are required. The mold for injection molding may be in the form of insert as is known in the art. Conventionally machines such as milling machines, electric discharge machining and the like are used to make metallic molds with a mirror finish in the device forming areas. These machined molds or mold inserts are preferred to obtain high number of copies of the desired devices. Polymer molds made of high temperature polymers such as polyimide, e.g. DuPont Kapton™, are also possible if high gloss and optical transparency in the devices are needed. In the case of Kapton molds, the negatives of the microfluidic features in the device are fabricated in the Kapton films using technique such as laser machining or photolithography and etching. A metallic frame defining the thickness of the device is used to enclose the resin during the molding process. Another sheet of Kapton film with or without microfluidic feature is used to cover the resin. This arrangement is used for compression molding. For injection molding, such a Kapton mold may also be used in the form of mold insert.

The cartridge (FIGS. 7 and 8) for applying the sealing pressure of the microfluidic device may be machined or injection molded. Strong engineering plastic such as glass-filled nylon or polyetherimide are preferred, although metallic cartridges or a combination of metal and plastic may be used.

The large width to depth ratio of the microfluidic volume may require support structures within the volume to prevent the top and bottom of the fluidic volume to collapse upon each other. The support structures may be columnar structures, which are integral parts of the inner surface of the top or the bottom of the fluidic volume. These columnar features may also be arranged along the length of the fluidic volume at regular intervals from side to side to form channel-like features to minimize sideway motion of the fluid inside the wide fluidic volume.

Figure 9:
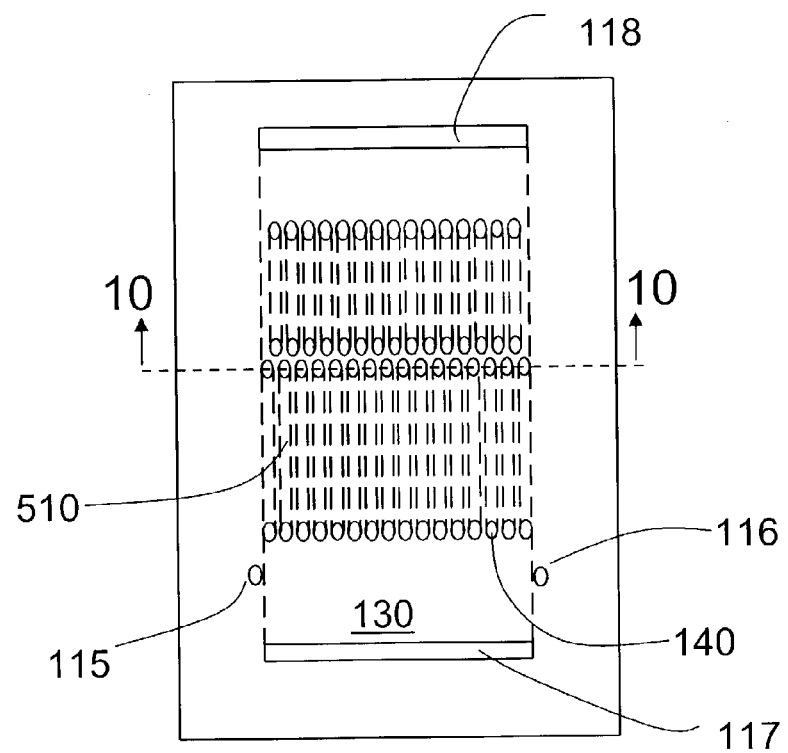
FIG. 9 is a top plan view of a microfluidic device according to a fourth embodiment and including channels that mate to the ports for sample selection so that the selected spot of sample may be conducted away from the fluidic volume.
Figure 10:
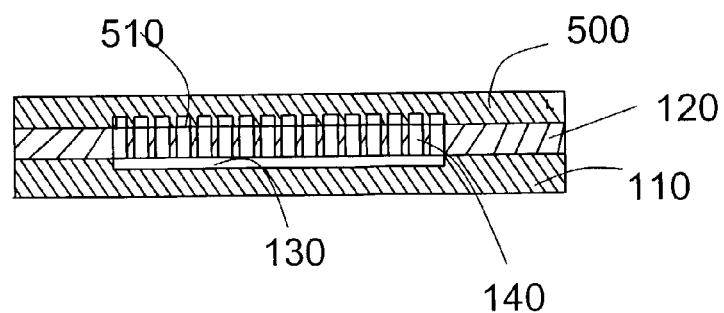
FIG. 10 is a cross-sectional view taken along the line 10—10 of FIG. 9.
Figure 11:
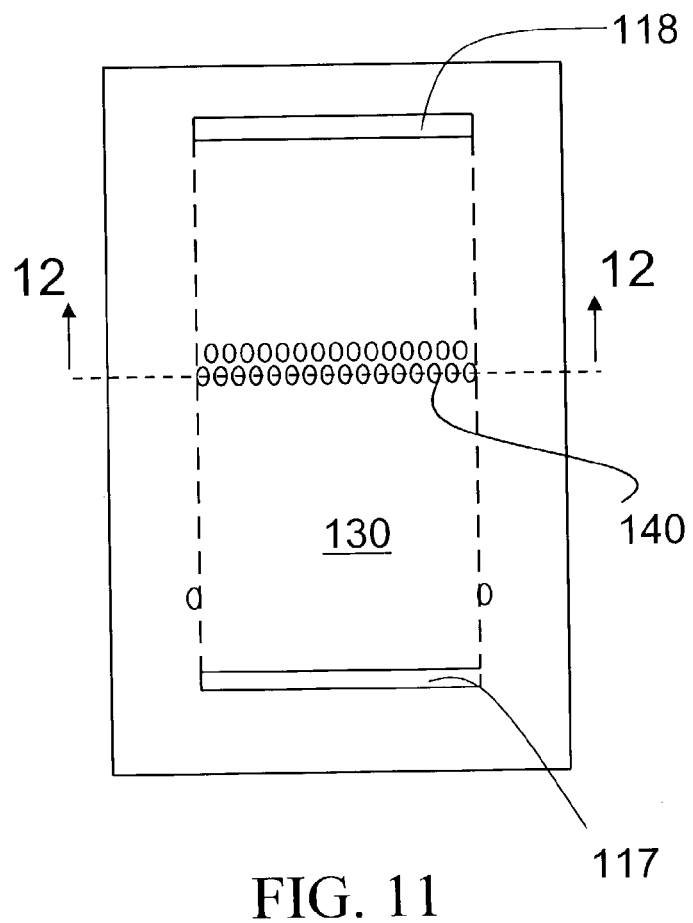
FIG. 11 is a top plan view of a microfluidic device according to a fifth embodiment where the routing mechanism is not through fabricated microfluidic channels, but rather capillaries that are inserted into the sample selection orifices.
Figure 12:
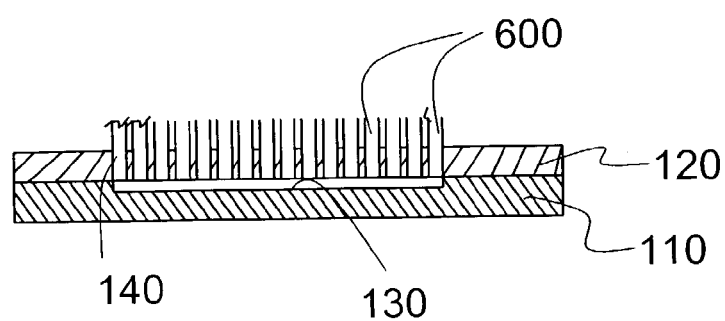
FIG. 12 is a cross-sectional view taken along the line 11—11 of FIG. 11.

The openings and ports in the microfluidic devices may be open to sample inlet and outlet devices external to the microfluidic device in this invention, or they may be open to another part of the same fluidic device. Or they may be input and output ports, or reservoirs where sample and sample waste may be stored on the device. FIGS. 9 and 10 show the embodiment where the sample selecting series of ports open into channels on a third substantially planar substrate. FIGS. 11 and 12 show the embodiment where the sample select ports open into capillaries that are inserted into the serious of openings.

The series of the sample select ports may be arranged in two or more rows, as shown in FIGS. 1, 3, 5, 9 and 11. The openings in the first row stagger those in the second row spatially as closely as possible. In this manner the openings access the entire width of the fluidic volume without any space along the width of the fluidic volume that is inaccessible by the openings.

Figure 13:
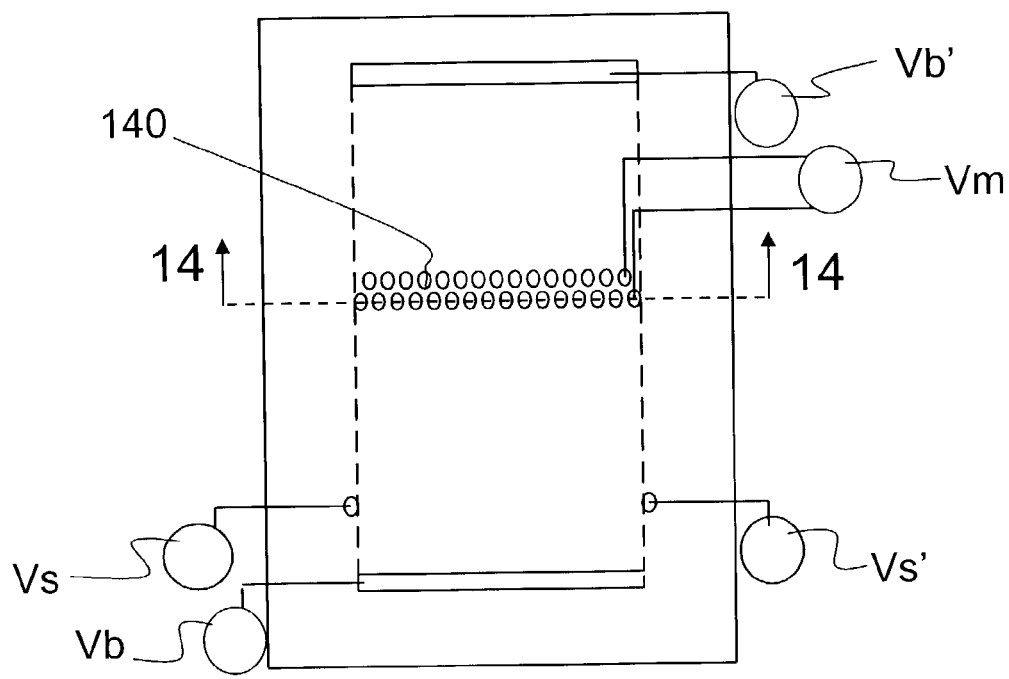
FIG. 13 is a top plan view of the microfluidic device of FIG. 11 showing the locations on the microfluidic device where voltages are applied to perform a two-dimensional separation operation.
Figure 14:
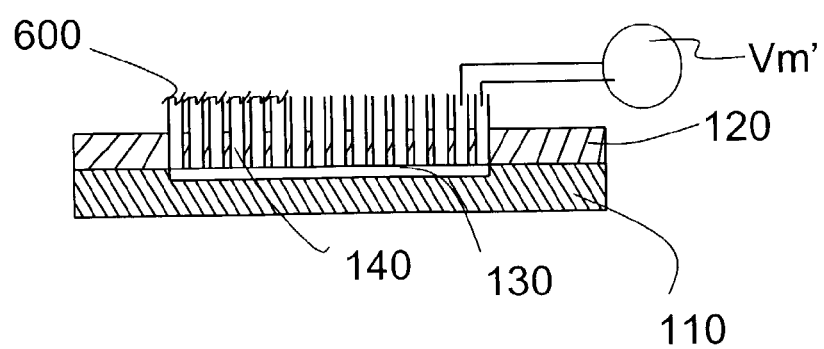
FIG. 14 is a cross-sectional view taken along the line 14—14 of FIG. 13.

In the application of proteins separation using this microfluidic device, along the length and width of the fluidic volume are disposed a plurality of metallic films or wires that are in contact with the fluids and particles within the fluidic volume and are also connectable to external electrical power supplies. In one embodiment, a metallic film or wire running the width of the fluidic volume is positioned around the midpoint of the length of the fluidic volume. Metal films or wires are also disposed in the openings for sample input and output. All the metallic components can be connected to external power supplies. FIGS. 13 and 14 show one such an embodiment.

The openings and ports in any of the previously described microfluidic devices can be open to sample inlet and outlet devices external to the microfluidic device itself, or they can be open to another part of the same microfluidic device. Alternatively, there can be input and output ports or reservoirs where sample and sample waste may be stored on the microfluidic device. FIGS. 9 and 10 illustrate an embodiment that is similar to the embodiment shown in FIGS. 1 and 2 except that a third planar substrate 500 is provided and is disposed on top of the second substrate 120. The second substrate 120 includes the plurality of sample selecting ports or openings 140 formed therethrough and in communication with the microfluidic cavity 130. The number and arrangement of the openings 140 varies according to the precise application. The third planar substrate 500 includes a plurality of channels 510 that are formed therein according to a predetermined pattern. In the illustrated embodiment, there are four rows of openings 140 with one channel 510 extending between one opening 140 of one row and another opening 140 of a next adjacent row. Thus, each of the openings 140 opens into one channel 150. FIGS. 11 and 12 show an alternative embodiment where the sample selecting ports or openings 140 of the second substrate 120 open into capillaries 600 that are disposed within the openings 140, to thereby permit sample to be injected or otherwise disposed in the openings 140 and then into the microfluidic cavity 130.

Figure 15:
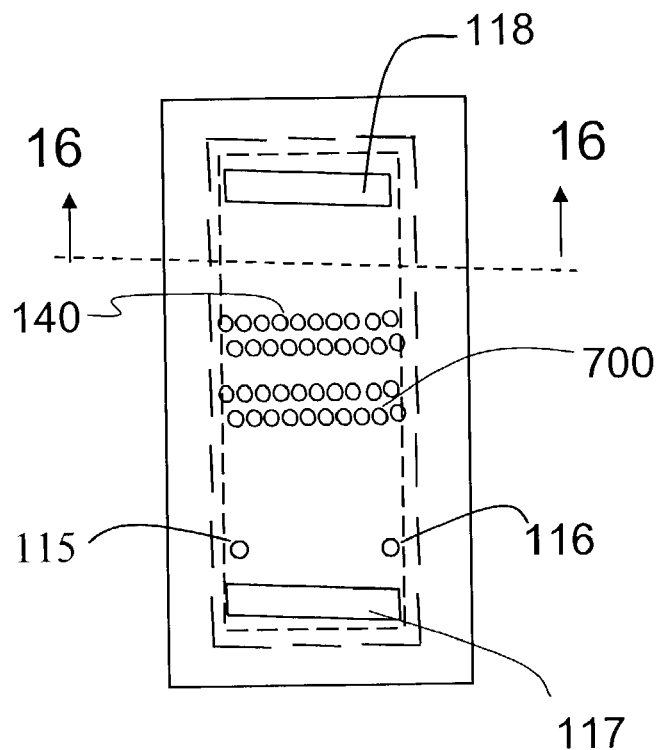
FIG. 15 is a top plan view of a microfluidic device according to another embodiment.
Figure 16:
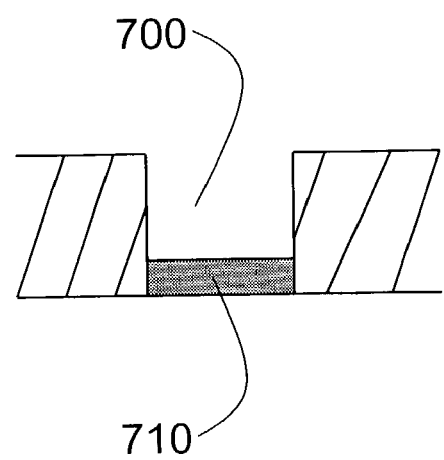
FIG. 16 is a cross-sectional view taken along the line 16—16 of FIG. 15.

An additional series of sample openings and ports placed between the buffer and gel input port 117 and sample selection ports 140 may also be used as optical windows for transmitting light into the microfluidic cavity 130 for optical detection. The openings in this series of ports are sealed with a polymer film which transmits light. The polymer film may be made of polyvinyl alcohol, hydroxymethylcellulose, a soluble Teflon-related polymer in solution, and the like. The film was cast from a solution of the polymer in the openings of the ports themselves. For example, a drop of 5% by weight of polyvinyl alcohol with a molecular weight of 100,000 may be placed inside an opening in the series of ports. Surface tension will keep the liquid polymer film stretched across the opening. When the liquid in the polymer solution has evaporated, a polymer film sealing the ports 700 that transmits ultraviolet light down to 200 nm may be obtained. This is especially useful for ultra-violet light transmission because most thermal plastics do not transmit ultra-violet light with wavelengths below 260 nm. FIG. 15 shows a device with the additional series of circular ports 700 in addition to the sample selection ports/openings 140. All the ports 700 are sealed by one or more polymer films 710 that transmit ultra-violet light. FIG. 16 shows the polymer film 710 sealing the port 700. For optical transmission detection through the microfluidic device, a corresponding series of ports similarly sealed by polymer films are placed directly across from the series of ports 700 in the second substrate. The thickness of the film is in the range of a few microns to 10's of microns.

The series of the sample selecting ports/openings 140 can be arranged in two or more rows as shown in FIGS. 1, 3, 5, 9, 11 and 13 or they can be arranged in an alternative pattern. The openings 140 in the first row stagger those in the second row spatially as closely as possible. In this manner the openings 140 access the entire width of the microfluidic cavity 130 without any space along the width of the microfluidic cavity 130 that is inaccessible by the openings 140.

In the application of protein separation using one of the present microfluidic devices, along the length and width of the microfluidic cavity are disposed a plurality of metallic films or wires or other conductive materials that are in contact with the fluids and particles within the microfluidic cavity 130 and are also connectable to external electrical power supplies. FIGS. 13 and 14 illustrate one embodiment and for purpose of illustration only, the microfluidic device 100 of FIGS. 1 and 2 is used to describe the present features. In FIG. 13, a metallic film or wire 700 running the width of the microfluidic cavity 130 is positioned around the midpoint of the length of the microfluidic cavity 130. Metal films or wires are also disposed in the openings for sample input and output. All the metallic components can be connected to external power supplies Vb, Vb', Vs, Vs', Vm and Vm'. Vb is the voltage applied to the buffer and gel input port 117; Vb' is the voltage applied to the buffer and gel output port 118; Vs is the voltage applied to the sample input port 115; Vs' is the voltage applied to the sample output port 116; Vm is the voltage applied to the sample selection region 140; and Vm' is the voltage applied to the distal ends of the channels or capillaries mated to the sample selection orifices. FIG. 14 illustrates the embodiment where capillaries 600 are used.

The fluidic volume is filled with at least one polymeric gel substance exemplified by but is not limited to polyacrylamide, SDS-gel, polyethylene oxide, hydroxypropylcellulose, hydroxymethylethylcellulose, and other hydroxyalkylcelluloses.

The fluidic volume may contain amphoteric ions along one side of the microfluidic volume so as to create a gradient of pH along the said side of the fluidic volume. The amphoteric ions may be dispersed in the gel or attached to the wall along the width of the microfluidic volume, between the sample input and sample output ports. The amphoteric ions may also be highly conjugated polymers such as polythiophene at different oxidation states.

For proteins separation, it may be desirable to select and collect a particular protein from the protein mixture for further processing and analysis with the sample select outlet orifices. The two rows of orifices may be placed in the proximity of the metal film electrode that runs across the width of the fluidic volume. The orifices are located in the bottom surface of the planar fluidic volume, or they may be located in the planar substrate that covers the planar fluidic volume. The orifices in each row are arranged so that the orifices in the two rows are staggered. The diameters of the orifices are in the range of 20 to a few hundred µm. The spacing between the orifices is less than the diameter of each orifice. Each orifice is connected to a channel that leads to other microfluidic features, such as one designed for desalting, or to an external surface through a spotter, which may be a nozzle or an elongated structure extending from the body of the substrate.

The substantially planar substrates are made of polymeric materials, preferably thermoplastics that are chemically pure without leachable additives, and optically transparent. Suitable polymers include polycyclic olefin polyolefin copolymers. Other suitable polymers include polymethylmethacrylate, polycarbonate and polystyrene. Optically opaque thermoplastics may also be used if optical detection of the analytes is carried out through optically transparent windows built into the substrates, or through quartz and other optically transparent capillaries inserted into the sample selection ports. The optically opaque thermoplastics may include but are not limited to polyamides such as Nylon®, liquid crystalline polymers, polyethylene, polypropylene, polybutylalcohol, polybutylalcohol and acrylates co-polymers, and any other thermoplastics with injection molding properties suitable for producing features with dimensions from 100 µm.

The substantially planar substrates making up the fluidic volume may also be of different non-conducting materials such as glass, quartz, ceramics and sapphire. The planar substrates may also be made of a mix of materials at least one of which is polymeric. Polymers suitable for being the substrates in this case may be elastomers such as polydimethylsiloxane, polyurethane and other silicone-based elastomers, or acrylate containing co-polymers such as Bynal®, Surlyn®, or polyalcohols.

The devices described herein are preferably fabricated with injection molding technology wherein a mold with the negative features of the desired microfluidic elements is used to reproduce multiple copies of the substrates with the desired microfluidic features. Compression molding and hot embossing are also suitable for small lot manufacturing.

The mold for injection molding or the device itself may be fabricated with conventional silicon-based microfabrication techniques, conventional machining with machine tools, laser machining, electric discharge machining, chemical etching of features defined by photolithography on semiconductor or metal substrates.

The present application also discloses a method for protein separation using the device disclosed herein. Referring to the device 200 in FIGS. 5 and 6, the microfluidic cavity 230 of the device 200 is filled through the buffer and gel input and output reservoirs 117 and 118, respectively, with an appropriate buffer and a gel chosen from the following, hydroxyethylmethylcellulose, polyethylene oxide, hydroxyalkylcelluloses, polyacrylamide and SDS gel. The whole microfluidic device 200 can be mounted on vibration isolation structures to minimize accidental motion of the fluid inside the microfluidic cavity 230.

The protein mixture, for example, a lysate from whole cells, fills the region between the sample input port 115 and sample output port 116 with amphoteric ions or highly conjugated polymers at various oxidation states. The protein mixture sample has been properly stained before being put into the sample inlet port 115. Proteins of different pKA values will be separated along the pKA gradient created by the amphoteric ions in a process known as isoelectric focusing.

Once the isoelectric focusing separation of the proteins is achieved, a voltage difference between the gel and buffer input port 117 and sample selection ports 140 is applied. Proteins that have been separated into bands according to their pKA along the width of the microfluidic device 200 will move towards the waste end (port 118) of the microfluidic device 200 by electrokinetic transport. The bands will not mix during the electrokinetic transport because of the laminar flow regime of the flow. Protein molecules of different mass/charge ratio will move at different speeds and will be separated.

Detection of the protein molecules after separation is carried out optically using conventional optical spectrophotometry at the location of the microfluidic cavity 130 a short distance before the sample selection ports 140.

If a particular spot of molecules is desired for further analysis, a voltage difference across the sample selection opening 140 to where the spot of molecules is closest and the distant end of the channel or capillary connected to the sample selection opening 140 is applied to drive the spot of molecules to a location outside of the microfluidic cavity 130 through channels 510 in FIG. 9, or capillaries 600 in FIG. 12. Spots of molecules that are not selected will continue to be pushed by the molecules, gel and buffer that are transported by electrokinetic motion to the buffer and gel waste port 118.

A method for protein separation in which the protein molecules are not chemically stained is also disclosed. The procedures for this method are similar to that described in above except that after the isoelectric focusing separation of the protein molecules has occurred, a voltage difference is applied across the buffer and gel input port 117 and the distal end of each of the capillary 600 inserted into each of the sample selection opening 140. The optical detection of the spots of molecules is carried out by shinning ultra-violet radiation of wavelength down to 200 nm onto the capillaries 600, which are made of quartz. The spot of molecules of interest may also be diverted to a collection device outside of the quartz capillary for further sample processing.

It is also possible to use protein samples already separated in a commercially available pKA strip (for example, one purchased from Biorad). In this method, the two substrates of the microfluidic device 200 as shown in FIGS. 5 and 6 are not assembled. The strip of pKa-separated proteins may be placed across the width of the microfluidic cavity 230 at the location of the sample input port 115 and sample output port 116 within the boundary of the raised walls 214. The width of the microfluidic cavity 230 bound by the raised walls 214 has the same width as the length of the strip chosen for the separation. The raised section 222 of the second substrate 220 is than inserted into the region bound by the raised walls 214 to form the microfluidic cavity 230. The assembled substrates 210, 220 containing the strip is pushed into a cartridge such as that shown in FIG. 7. The ridges in the cartridge press onto the raised walls boundary to create a liquid-tight seal. The distance between the ridges from the top and bottom surfaces of the cartridge is such that it is slightly less than the thickness of the two substrates 210, 220 of the device 200 after assembly. Gel and buffer are then placed in the input reservoir or port 117 and buffer output reservoir or port 118. A voltage difference is applied to the buffer input port 117 and output port 118 to start the separation process based on molecular sizes.

The following examples are used for illustration purposes only. The exact procedures may be varied by one skilled in the art according to this disclosure.

EXAMPLES

Example 1

A microfluidic device with a microfluidic volume exemplified by that in FIG. 6 was fabricated with a metallic molds with the negative of the microfluidic features in a compression molding press. One mold contains the negative of the lid insert, which was 1.905 cm in width and 150 microns in height and about 5 cm long, and the access ports for sample and buffers, etc. and other channel features that facilitate optical detection. The other mold contains the negative of the access ports which were about 368 microns in diameter, and the negative of the raised walls structures which were about 200 microns in height and about 0.75 mm thick. The length and width of the rectangular structure formed by the negative of the raised walls would accept the insert with a 25 microns tolerance. The surfaces of the molds were polished to obtain a mirror finish. The polymer is Topas™ grade 8007. 50 microns thick Kapton (DuPont) sheets were put on one side of each mold in the compression molding press to obtain optical transparency and gloss in the device. The molding was carried out at about 235 F for 10 minutes and cooled to 171 F in the press. When the two substrates were made, the insert ridge is inserted into the region enclosed by the raised walls, and quartz capillaries wrapped in polyimide with an overall outside diameter of 360 microns were inserted into the access ports formed during molding. The two assembled substrates are inserted into a plastic cartridge was hinged with a rectangular raised structure that match the dimensions of the raised walls in the microfluidic device. When the two leaves of the hinged cartridge were closed and held tight by fasteners, such the assembled substrate is held snugly inside. The cartridge had a large opening just smaller than the microfluidic volume so that all the fluid input and output ports were accessible. A phosphate buffer was pumped pneumatically into the microfluidic volume through one of the buffer reservoir, and the liquid was observed to be contained inside the microfluidic volume without leakage.

Example 2

The same design of the device was fabricated using laser-machined Kapton films as the mold insert. The support of the Kapton films were aluminum pieces with features for locating the Kapton mold properly on the aluminum support. The molding and assembly processes was carried identically as in Example 1

Example 3

A microfluidic device with microfluidic feature with a width of 1.905 cm and a length of 5 cm and a depth of 150 microns as designed by raised walls on one substrate and an insert in the lid was fabricated similarly as described in Example 1 using either compressin molding as described in Example 1 or injection molding with a mold with a mirror finish and the same polymer. The Topas substrates were each 1/16" thick. Various sample access ports were fabricated at the same time. The two pieces were assembled by inserting the lid structure into the raised walls region. The clamping edges of the butterfly clips were placed directly over the raised walls at several locations. A liquid phosphate buffer was placed inside the microfluidic volume was contained inside the raised walls without leakage. The clips were then removed and the substrates taken apart to dry up the phosphate buffer with a wipe. On the raised walls side of the substrate, three drops of water 1 microliter in volume were placed apart from each other with a graduated syringe. Each drop formed a round dome shape on the surface within the raised wall region. The lid with the insert was placed within the raised walls and the dome shape drops were flattened into circles. The clips were again put in placed over the raised walls and the areas of each droplet of the water. The depth of the microfluidic volume was verified to be about 150 microns. Additional clips were now placed on the outer surface of the region enclosed by the raised walls. The positions of these additional clips were varied until the areas of the each circular spot formed by the water drops were approximately doubled. The depth of the resulted microfluidic volume was approximately ¼ of its original value of 150 microns.

What is claimed is:

1. A microfluidic device comprising:
   first and second substrates;
   a microfluidic cavity formed in one of the first and second substrates, the microfluidic cavity having a width (W) and a depth (D), wherein the other of the first and second substrates encloses the microfluidic cavity and a width (W) to depth (D) ratio is at least 100 with the depth (D) being from about 10 μm to about 150 μm;
   a plurality of ports formed in the other of the first and second substrates to permit access to the microfluidic cavity; and
   a third substrate disposed on the second substrate and including microchannels formed therein, the microchannels being formed so that a plurality of ports formed in the second substrate for sample selection and sample output communicate therewith.

2. The microfluidic device of claim 1, wherein the plurality of ports formed in the second substrate for sample selection and sample output are arranged in rows, each microchannel in communication with and extending between one port formed in one row and another port in a next adjacent row.

3. The microfluidic device of claim 1, further including:
   a plurality of capillaries that are disposed within a plurality of ports formed in the second substrate for sample selection and sample output.

4. A microfluidic device for achieving protein separation based on charge and molecular weight or size, the device comprising:
   a first substrate having a raised structure protruding from a first face of the first substrate, the raised structure partially defining a microfluidic cavity;
   a second substrate having a raised section protruding from a first face of the second section, the raised section having a shape and dimensions complementary to the microfluidic cavity to permit the raised section to be received between the raised structure to enclose the microfluidic cavity, the raised section sealing with the raised structure in a liquid tight manner while still permitting removal of the first and second substrates from one another, the microfluidic cavity having a width (W) and a depth (D); and
   sample inlet and outlet ports formed in the second substrate in communication with the microfluidic cavity;
   buffer and gel input and output ports formed in the second substrate in communication with the microfluidic cavity; and
   a plurality of ports formed in the second substrate for sample selection and sample output.

5. The microfluidic device of claim 4, wherein the raised structure comprises a raised wall arranged to have a preselected shape that is the same shape as the raised section.

6. The microfluidic device of claim 5, wherein the preselected shape is rectangular.

7. The microfluidic device of claim 4, wherein the raised structure has an upper edge that seats against the first face of the second substrate when the first and second substrates mate together, the depth (D) being defined as the distance from a face of the raised section to the first face of the first substrate.

8. The microfluidic device of claim 4, wherein there is a single microfluidic cavity.

9. The microfluidic device of claim 4, wherein the buffer and gel input port extends substantially the width of the microfluidic cavity and is formed at one end thereof, the buffer and gel input port extending substantially the width of the microfluidic cavity at an opposite end thereof.

10. The microfluidic device of claim 9, wherein the plurality of ports formed in the second substrate for sample selection and sample output is disposed between the buffer and gel input and output ports.

11. The microfluidic device of claim 10, wherein the plurality of ports formed in the second substrate for sample selection and sample output is arranged in at least two rows, each row being staggered from each next adjacent row.

12. The microfluidic device of claim 4, wherein a width (W) to depth (D) ratio of the microfluidic cavity is at least 100 with the depth (D) being from about 10 μm to about 150 μm.

13. The microfluidic device of claim 4, further including:
   a plurality of UV transmission ports formed in the second substrate between the buffer and gel input and output ports; and one or more polymer films that transmit UV light being disposed within or across the UV transmission ports.

14. The microfluidic device of claim 13, wherein one or more of the polymer films transmits ultraviolet light down to 200 nm.

15. A microfluidic kit for performing protein separation based on charge and molecular weight or size, the microfluidic kit comprising:
a microfluidic device according to claim 5; and
a cartridge for applying pressure to the microfluidic device to ensure sealing of the microfluidic cavity, the cartridge having a body including a cavity formed therein, the body having an opening forming an entrance to the cavity for receiving the microfluidic device, wherein a plurality of longitudinal and transverse rails are formed within the cavity and are arranged according to the construction of a raised wall of the microfluidic device such that when the microfluidic device is received within the cartridge, the longitudinal and transverse rails exert mechanical pressure on areas of the raised structure of the microfluidic device to ensure a liquid tight sealing of the microfluidic cavity.

16. The microfluidic kit of claim 15, wherein the cartridge includes a window formed in one wall opening into the microfluidic cavity to permit access to the second substrate of the microfluidic device so that materials can be introduced and withdrawn from the microfluidic cavity and detection techniques can be performed.

17. The microfluidic kit of claim 15, wherein the body includes a top wall and bottom wall and two end walls with the top wall having a first pair of longitudinal rails formed thereon and the bottom wall having a second pair of longitudinal rails formed thereon and wherein a pair of transverse rails extend across each of the top and bottom walls between respective longitudinal rails, the microfluidic device being received between the pairs of longitudinal and transverse rails.

18. The microfluidic kit of claim 17, wherein each longitudinal rail has a chamfered section near the open end of the body to assist in receiving the microfluidic device into the cartridge cavity.

19. A microfluidic kit for performing protein separation based on charge and molecular weight or size, the microfluidic kit comprising:

a microfluidic device according to claim 4; and
a cartridge for applying pressure to the microfluidic device to ensure sealing of the microfluidic cavity, the cartridge having a first part and a second part hingedly connected to the first part to permit the cartridge to be positionable between open and closed positions, the first part having a raised feature formed on one face thereof and arranged according to the construction of the raised structure of the microfluidic device such that when the microfluidic device is received on a face of the second part and the first and second parts are closed together, the raised feature exerts mechanical pressure on areas of the raised structure of the microfluidic device to ensure a liquid tight sealing of the microfluidic cavity between the first and second substrates.

20. The microfluidic kit of claim 19, wherein the first part has a window formed therein within the boundaries of the raised feature so that materials can be introduced and withdrawn from the microfluidic cavity and detection techniques can be performed.

21. A method for separating protein molecules that are free of any chemical stain, the method comprising the steps of:
providing the microfluidic device of claim 4 in a disassembled state where the first and second substrates are separated from one another;
placing a pKa strip within the raised structure of the first substrate such that it extends across the width (W) of the microfluidic cavity;
assembling the first and second substrates such that the raised section is received within boundaries of the raised structure to define and seal the microfluidic cavity;
inserting the microfluidic device into the cartridge of claim 15 to create the liquid-tight seal of the microfluidic cavity;
disposing gel and buffer material through at least one of the gel and buffer input and output ports so that it travels into the microfluidic cavity; and
applying a voltage difference to the buffer and gel input port and the buffer and gel output port to begin separation of the protein molecules based on molecular sizes.

* * * * *